(12) United States Patent
Varda

(10) Patent No.: US 11,304,846 B2
(45) Date of Patent: Apr. 19, 2022

(54) HILOTHERAPY SHOULDER WRAP AND STRAP ASSEMBLY

(71) Applicant: Anthony Terence Varda, South Bend, IN (US)

(72) Inventor: Anthony Terence Varda, South Bend, IN (US)

(*) Notice: Subject to any disclaimer, the term of this patent is extended or adjusted under 35 U.S.C. 154(b) by 182 days.

(21) Appl. No.: 16/683,061

(22) Filed: Nov. 13, 2019

(65) Prior Publication Data

US 2020/0146879 A1 May 14, 2020

Related U.S. Application Data

(60) Provisional application No. 62/760,747, filed on Nov. 13, 2018.

(51) Int. Cl.
*A61F 7/00* (2006.01)
*A61F 7/02* (2006.01)

(52) U.S. Cl.
CPC ........ *A61F 7/02* (2013.01); *A61F 2007/0228* (2013.01); *A61F 2007/0231* (2013.01); *A61F 2007/0279* (2013.01)

(58) Field of Classification Search
CPC ................ A61F 7/02; A61F 2007/0228; A61F 2007/0231; A61F 2007/0279
See application file for complete search history.

(56) References Cited

U.S. PATENT DOCUMENTS

| 5,334,132 A * | 8/1994 | Burkhead | A61F 5/3738 602/4 |
| 5,538,015 A * | 7/1996 | Paulson | A61F 5/0118 128/869 |
| 5,569,172 A * | 10/1996 | Padden | A61F 5/3753 128/878 |
| 6,083,256 A * | 7/2000 | Der Ovanesian | F28D 20/02 607/114 |
| 6,945,988 B1 * | 9/2005 | Jones | A61F 7/10 607/108 |
| 7,244,239 B2 * | 7/2007 | Howard | A61F 5/3753 128/878 |
| 10,179,075 B1 * | 1/2019 | Hickling | A61F 13/046 |
| 2005/0273026 A1 * | 12/2005 | Howard | A61F 5/3753 602/20 |
| 2007/0255187 A1 * | 11/2007 | Branch | A61H 7/001 601/15 |

* cited by examiner

*Primary Examiner* — Steven O Douglas
(74) *Attorney, Agent, or Firm* — Crump Law P.C.

(57) ABSTRACT

The hilotherapy wrap includes a conventional removable internal water bladder, an exterior cloth cover enclosing the bladder and a detachable strap assembly that allows the wrap to be donned and doffed by the user without assistance and using only one arm. The strap assembly includes a pair of elastic straps detachably connected to the cover by hook and loop fasteners affixed to a strap anchor and one of the strap ends. The strap assembly also includes a quick connect buckles and a slide or D-ring that allows both ends of the straps to be connected to the cover before tensioned snugly around the user.

11 Claims, 6 Drawing Sheets

HILOTHERAPY SHOULDER WRAP AND STRAP ASSEMBLY

This application claims the benefit of U.S. Provisional Application No. 62/760,747 filed Nov. 13, 2018, the disclosure of which is hereby incorporated by reference.

This invention relates to hilotherapy, and in particular, a cold compression shoulder wrap and strap assembly used in hilotherapy.

BACKGROUND AND SUMMARY OF THE INVENTION

Hilotherapy, also known as cold compression therapy, combines two of the principles of rest, ice, compression, elevation to reduce pain and swelling from a sports or activity injury to soft tissues and is recommended by orthopedic surgeons following surgery. Hilotherapy is especially useful for sprains, strains, pulled muscles and pulled ligaments. Hilotherapy involves the use of continuous cold therapy devices (also called ice machines) which circulate ice water through a pad applied to the injured area or body part.

Hilotherapy devices use chilled water to decrease the local temperature of tissue. Hilotherapy devices typically consist of cold water bladders configured into a compression wrap, typically in the form of pads, cuffs and sleeves for application to particular body parts and areas and an active cold water circulating device or passive, non-circulating water reservoir. The compression wraps are strapped to or worn by a user and generally can be used with either active circulating devices or passive non-circulating reservoirs. Passive, non-circulating reservoirs typically consist of an insulated container filled with iced water that is attached to a compressive cuff. When the container is raised, the water fills and pressurizes the pad or sleeve. The amount of pressure is proportional to the height of the container. When body heat warms the water within the pad, cuff or sleeve, the container is lowered and the water drains out. The container is then raised above the affected limb and cold water refills the compressive pad, cuff or sleeve. Active, circulating cooling devices use pumps to automatically circulate cold water and provide pneumatic compression to the compression wrap.

In hilotherapy, cold compression wraps, as well as, conventional ice packs use adjustable elastic straps to hold the wraps and packs to the user and aid in compression over the injured areas. The ends of these elastic straps typically use hook and loop fasteners that adhere to the wrap body to provide a quick detachable interface. While convenient, the elasticity of the straps and their hook and loop interface often makes it difficult for a user to don the wraps without assistance in certain applications. This is particularly true for shoulder injuries. Cold compression wraps designed for shoulder injuries, use elastic straps that are stretched around the torso to hold the wrap in place. The strap ends can be placed by hook and loop fasteners and positioned to adjust the fit and compression. With a shoulder injury, it is often difficult don the wrap holding it in place about the shoulder while reaching and adjusting the ends of the elastic straps, particularly without assistance or the use of both arms. When one end of the strap is detached from the wrap body for repositioning, the elasticity of the strap pulls on the wrap shifting it about the user's shoulder. Often the injury and absence of full arm articulation prevents the user from holding the wrap body in position while reattaching the strap ends without assistance.

The cold compression wrap of this invention can be donned by a user without assistance even when the user has limited use of either arms or the use of only one arm. The wrap consists of a conventional removable internal water bladder, an exterior cloth cover enclosing the bladder and a detachable strap assembly that allows the wrap to be donned and doffed by the user without assistance and using only one arm. The strap assembly includes a pair of elastic straps detachably connected to the cover by hook and loop fasteners affixed to a strap anchor and one of the strap ends. The strap assembly also includes quick connect buckles and a slide or D-ring that allows both ends of the straps to be connected to the cover before tensioned snugly around the user. With both ends of the elastic straps connected to the cover with the straps loosely wrapped around the user, the wrap can be donned and properly positioned atop the shoulder. Since the straps are connected to opposite side of the cover before tensioning, the hilotherapy wrap is held in place as the elastic straps are cinched down preventing the wrap from shifting about the user.

The above described features and advantages, as well as others, will become more readily apparent to those of ordinary skill in the art by reference to the following detailed description and accompanying drawings.

BRIEF DESCRIPTION OF THE DRAWINGS

The present invention may take form in various system and method components and arrangement of system and method components. The drawings are only for purposes of illustrating exemplary embodiments and are not to be construed as limiting the invention. The drawings illustrate the present invention, in which.

DESCRIPTION OF THE PREFERRED EMBODIMENT

Figure 1:
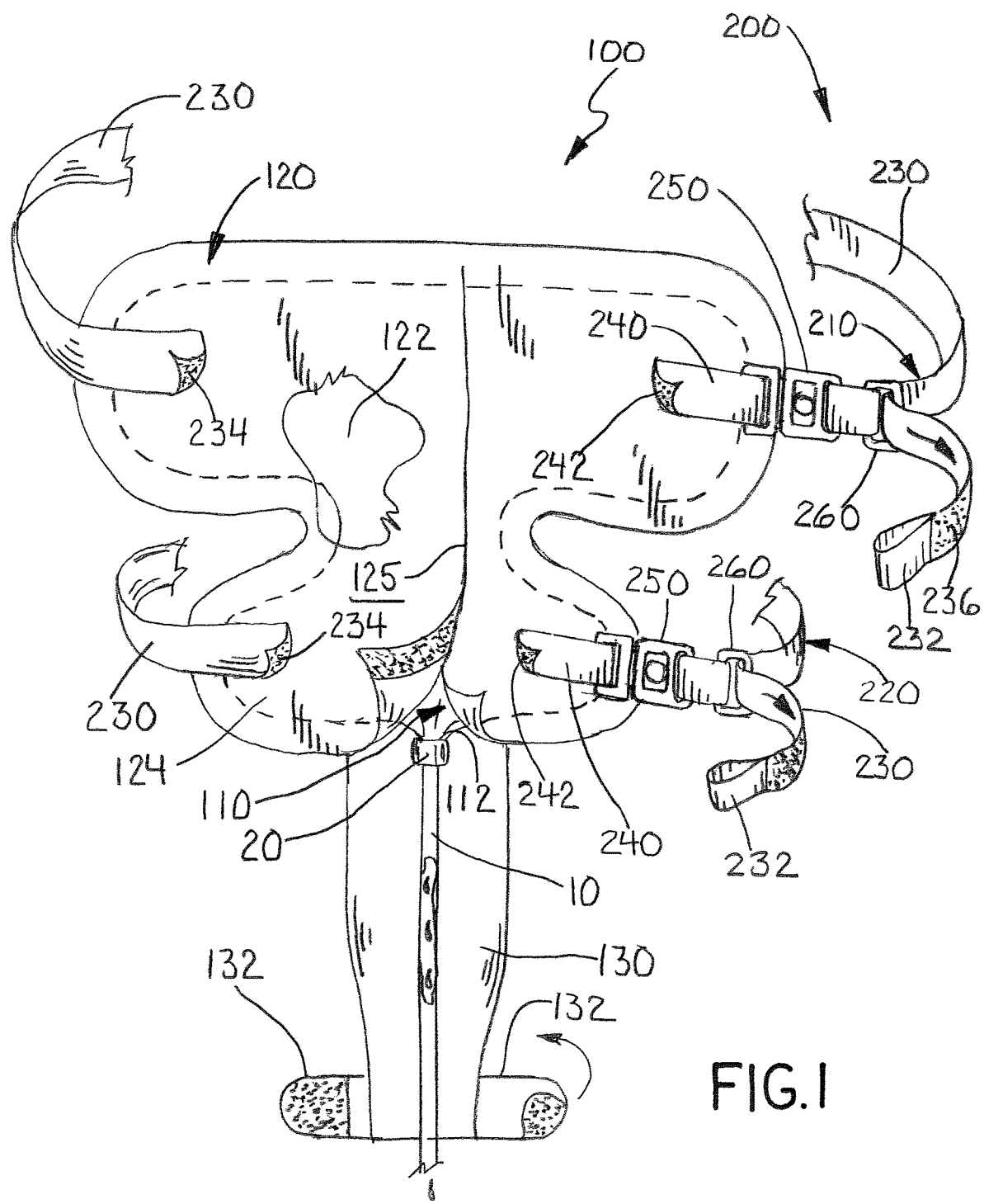
FIG. 1 is a plan view of a conventional hilotherapy shoulder wrap using an exemplary embodiment of the strap assembly of this invention.

In the following detailed description of the preferred embodiments, reference is made to the accompanying drawings that form a part hereof, and in which is shown by way of illustration specific preferred embodiments in which the invention may be practiced. These embodiments are described in sufficient detail to enable those skilled in the art to practice the invention, and it is understood that other embodiments may be utilized and that logical, structural, mechanical, electrical, and chemical changes may be made without departing from the spirit or scope of the invention. To avoid detail not necessary to enable those skilled in the art to practice the invention, the description may omit certain information known to those skilled in the art. The following detailed description is, therefore, not to be taken in a limiting sense, and the scope of the present invention is defined only by the appended claims.

Referring now to the drawings, FIGS. 1-7 illustrate an exemplary embodiment of the cold compression wrap of this invention, which is designated generally as reference numeral 100. As illustrated, wrap 100 is configured as a cold compression shoulder wrap for the hilotherapy treatment of shoulder injuries, where use and range of motion of one arm or shoulder is often limited. Shoulder wrap 100 generally consists of a conventional removable internal water bladder 110, an exterior cloth cover 120 enclosing the bladder and a detachable strap assembly 200. Strap assembly 200 allows wrap 100 to be donned and doffed by the user without assistance and using only one arm.

Although illustrated as a shoulder wrap, the teachings of this invention may be applied to other types of cold compression wraps or pads and strap interfaces used for other body parts and areas, such as a knee cuff, ankle boot or limb sleeve. Shoulder wrap 100 is also designed and adapted for use in hilotherapy with either active or passive cold water circulation hilotherapy devices (not shown), which provide water flow through a detachable fluid line (10) and connector (20). It should be noted that the teachings of this invention, particularly the strap assembly are also readily applicable to ice packs and other cold compression wraps.

Removable internal water bladder 110 is of conventional design and of the type used for covering the top of the shoulder and upper arm. Bladder 110 is shaped to have two large lobs designed to overlie the top of the shoulder, pectoral and deltoid areas, and two smaller lobs intended to cover and overlie the upper arm and bicep/tricep areas. Bladder 110 includes a fluid port 112 for providing fluid communication between fluid line 10 and the circulating device or reservoir. Generally, fluid port 112 is in the form of a detachable coupling mated to connector 20. Such couplings are common and well known in the industry.

Cover 120 is a fabric covering configured to removably receive bladder 110. Cover 120 is shaped to have two large pocket sections that receive the large lobs of bladder 110 and two small pocket sections that receive the small lobs of bladder 110. Cover 120 includes complimentary inner facing and outer facing panels 122 and 124 sewn or bonded together around their peripheral edges. Outer panel 124 has a hemmed central opening 125 detachably joined by overlying strips of hook and loop fastener tape, which facilitates the removal of bladder 110 from cover 120. Cover 120 also includes a fluid line flap panel 130 that extends from the main body of cover 120. Flap panel 130 is an elongated section of fabric material designed to underlie fluid line 10. The flap panel 130 provides a cloth barrier between the user's arm and fluid line 10, which often draws condensation that soaks into the user's clothing and bandages. Flap panel 130 includes a pair of hook and loop retention tabs 132, which help secure fluid line 10.

Cover panels 122 and 124 are constructed of a suitable fabric or cloth, which is selected to be pliable for conforming to the shoulder and arm, easily cleaned and to have a soft gentle hand for application directly to the skin. Generally, the fabric or cloth from which outer facing panel 124 is constructed is selected so that hook fastener patches and backing readily adhere thereto. In other exemplary embodiment, cover 120 may have patch section of loop material sewn or bonded to the outer facing surface at various locations to receive mating hook fastener patches and backings.

Strap Assembly 200 includes an elastic torso strap set 210 and a bicep strap set 220. Strap sets 210 and 220 differ only the length of the band with torso strap set 210 being dimensioned to wrap around a user's torso and bicep strap set 220 being dimensions to wrap around the user's biceps and upper arm. Torso strap set 210 detachably secure to the large pocket section of cover 120 which encloses the large lobs of bladder 110. Bicep strap set 220 detachably secure to the small pocket sections of cover 120 which encloses the small lobs of bladder 110.

Each strap set 210 and 220 includes a length of elastic webbing or band fashioned into a elongated band or strapping 230. The elasticity of straps 210 and 220 provides freedom of movement while securely holding wrap 100 in place about the user. Each length of strapping 230 terminates at one end in a strap loop 232. Each length of strapping 230 also has a hook fastener backing 234 at the one end and adjacent sections of hook and loop material 236 at the looped end, which allows the strap to adhere to itself when overlapped. The hook fastener backings 234 allows that end of each straps 210 and 220 to be detachably affixed to the outer facing surface of cover 120 and to be selectively positioned at any orientation and location on the cover.

Each strap set 210 and 220 also includes a strap anchor 240, quick disconnect coupler 250 and a slide or D-ring 260 for each strap 210 and 220. Slide or D-ring 260 receives the looped end of straps 230 and allows the user to cinch the strap down around the user's torso or bicep. Slide or D-rings 260 are of conventional design and function and are commonly known and commercially available in a variety of forms and from various manufacturers. Couplers 250 may take the form of any conventional quick-connect buckle, such as those manufactured by ITW Nexus of Frankfort, Ill. Each coupler 250 includes a mating male and female component and allows the user to quickly doff shoulder wrap 100. One of the mating components of coupler 250 is connected to slide 260 by a short length of webbing. Strap anchor 240 is a short length of webbing affixed to the other mating components of coupler 250. Strap anchor 240 has a hook fastener backing 242 that allows the anchor to be detachably affixed to cover 120 in the same fashion as backing 234.

Figure 2:
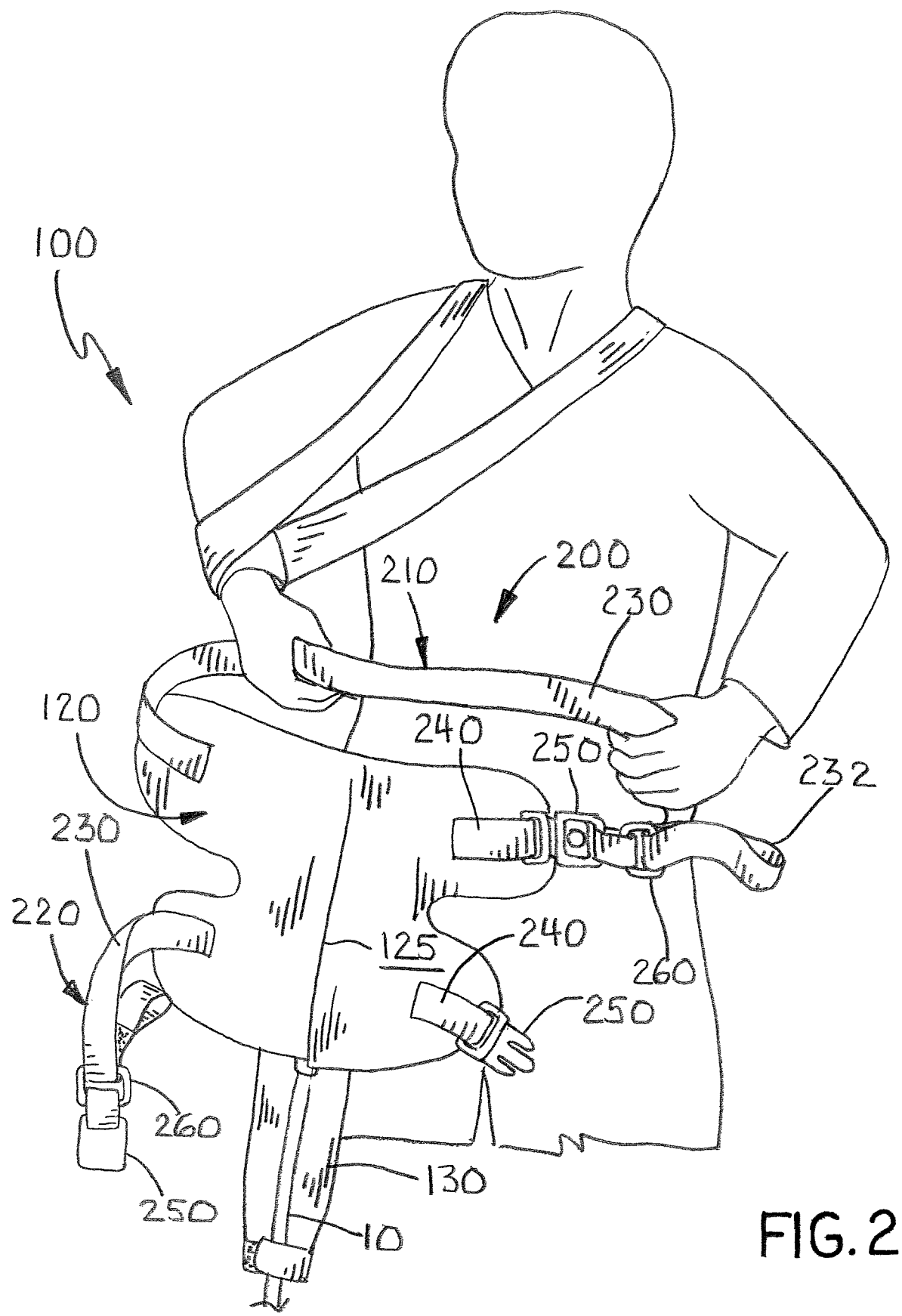
FIG. 2 is a front perspective view of a user holding the hilotherapy shoulder wrap of FIG. 1 in preparation of donning the wrap.
Figure 3:
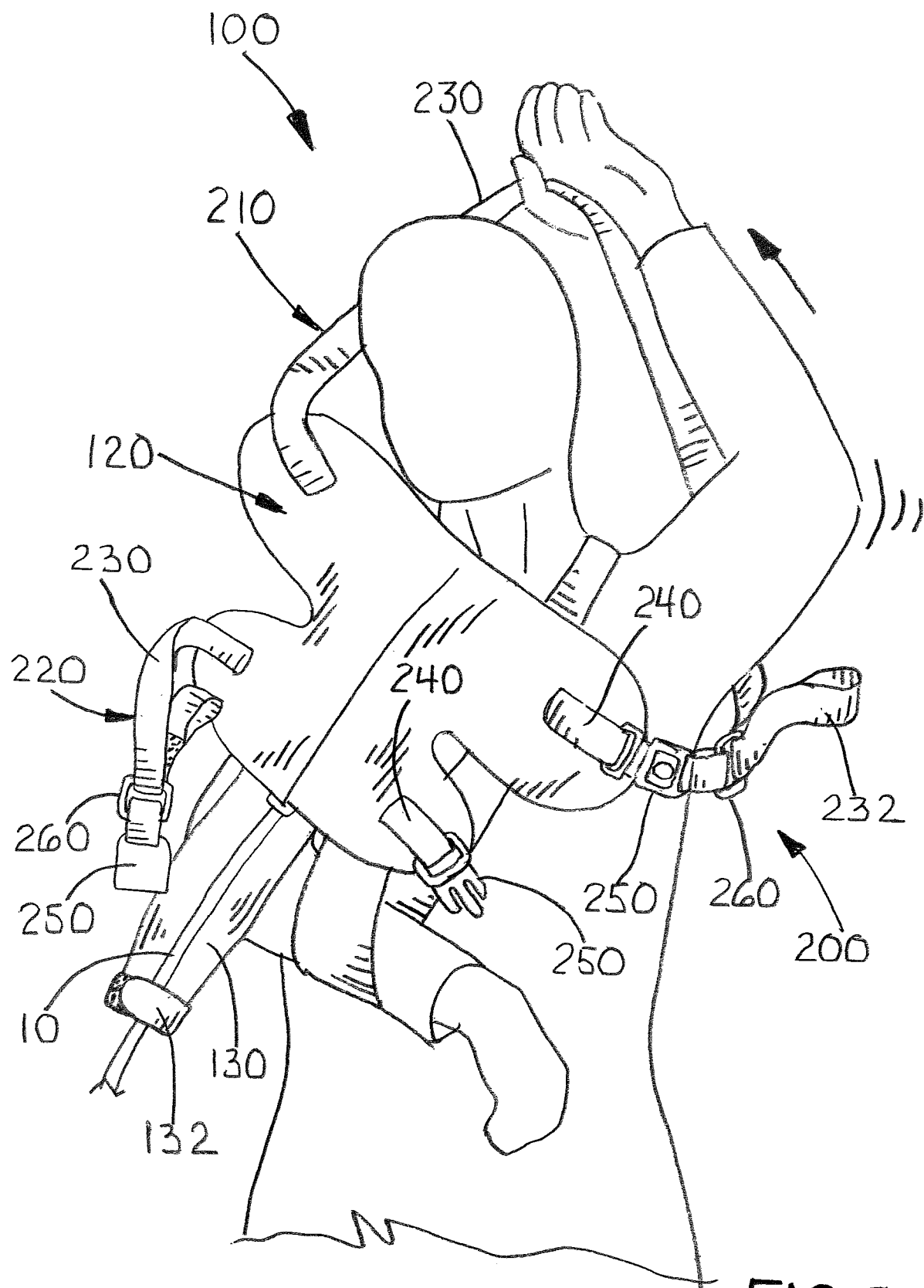
FIG. 3 is a front perspective view of a user raising the hilotherapy shoulder wrap of FIG. 1 overhead to don the wrap.
Figure 4:
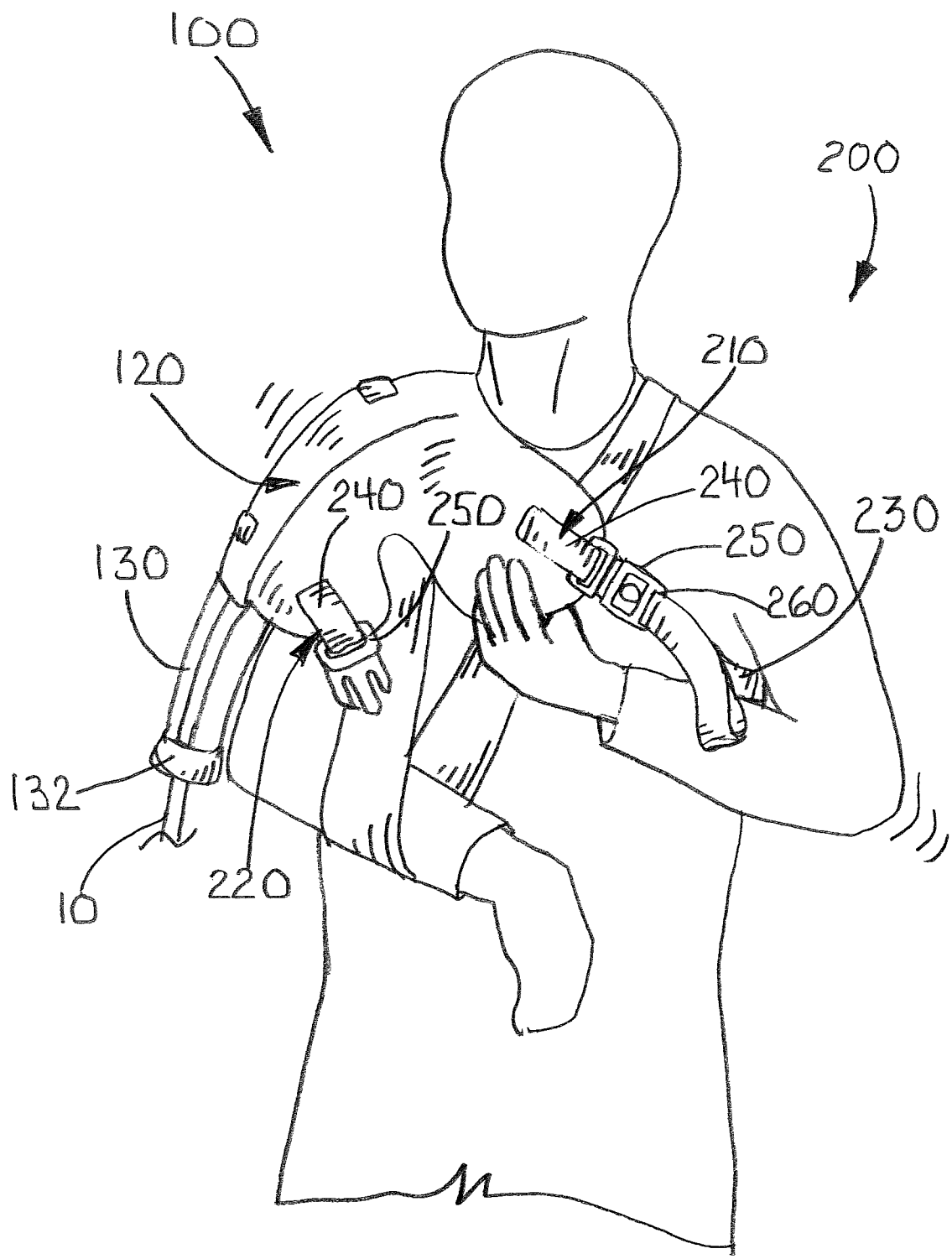
FIG. 4 is a front perspective view of a user positioning the hilotherapy shoulder wrap of FIG. 1 about the shoulder.
Figure 5:
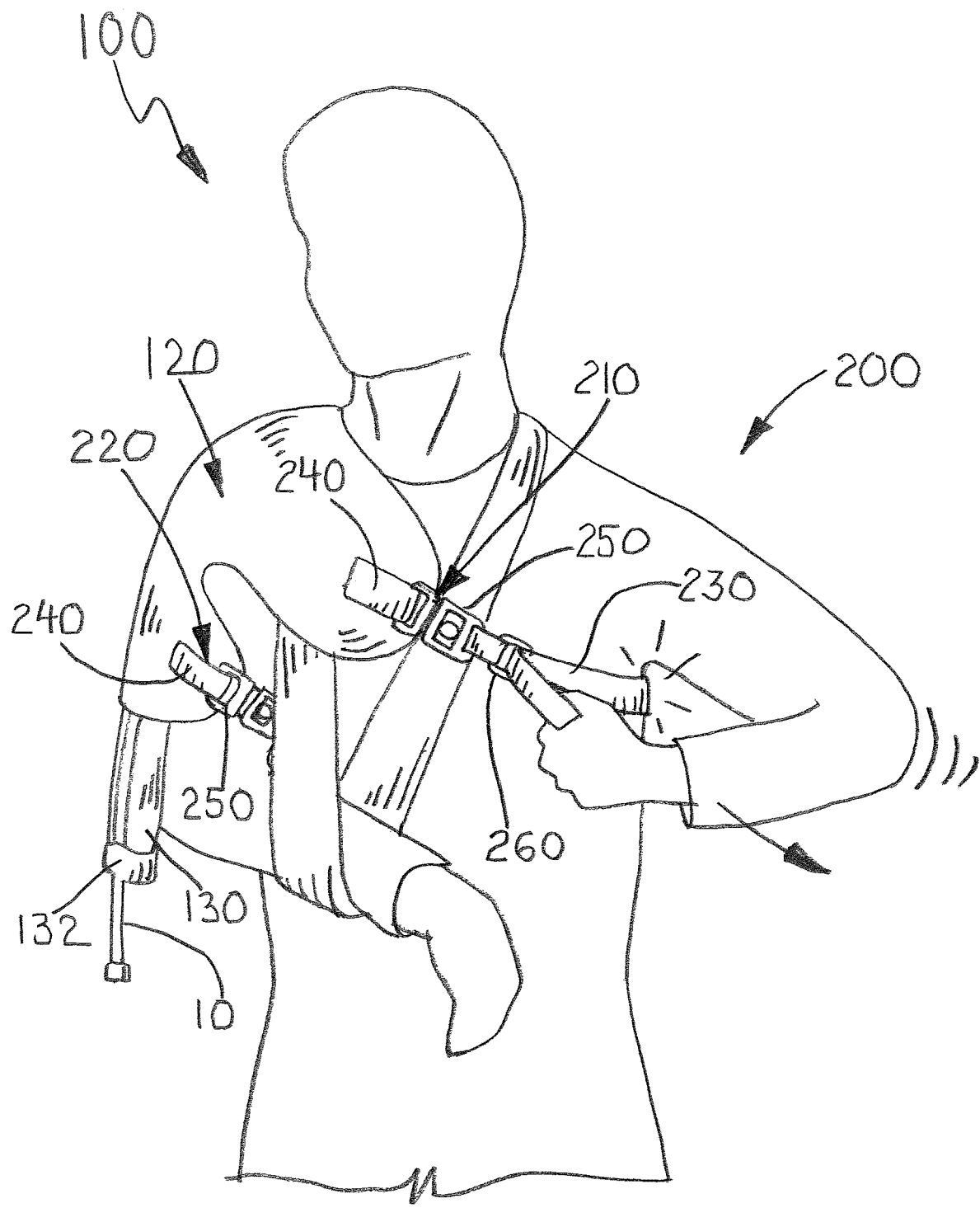
FIG. 5 is a front perspective view of a user tightening the torso strap of hilotherapy shoulder wrap of FIG. 1.
Figure 6:
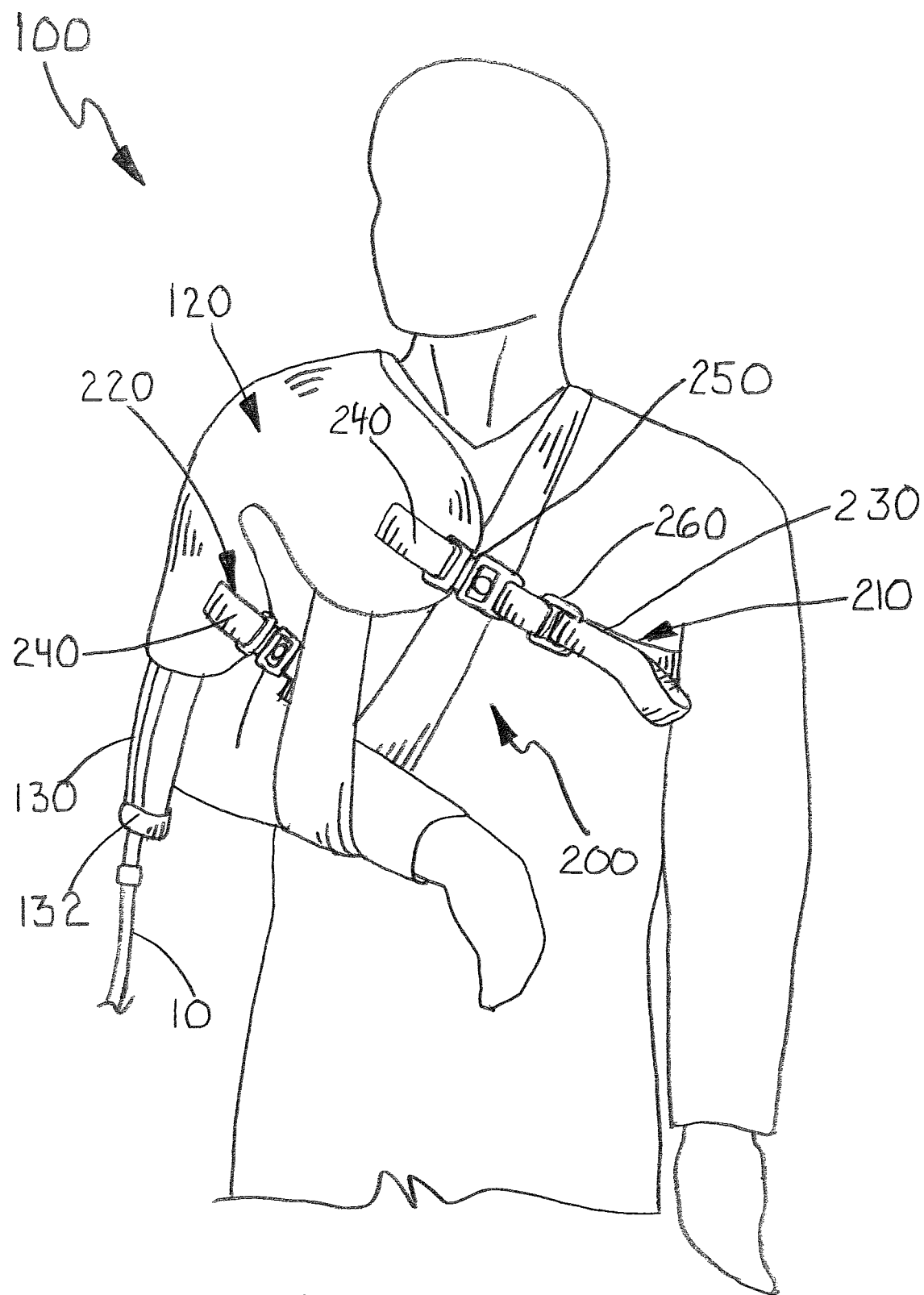
FIG. 6 is a front perspective view of a user connecting the fluid line to the hilotherapy shoulder wrap of FIG. 1.

FIGS. 2-7, illustrate the use of shoulder wrap 100. To don shoulder wrap 100, bladder 110 is first inserted into cover 120 and strap assembly 200 is affixed to the outer facing panel of the cover in the desired locations (FIG. 2). As shown, hook fastener backing 234 first secures one end of strap sets 210 and 220 to cover 120. Strap anchors 140 are also initially affixed to cover 120 before donning pad 100 and the looped ends of strap lengths 230 are inserted through slide or D-ring 260. The mating components of coupler 250 may also be connected or disconnected for donning as necessary. To don, user gently positions pad atop the injured shoulder with torso strap set 210 extending loosely around the user's torso (FIG. 3). Typically, coupler 250 of both torso strap 210 and bicep strap 220 are disconnect to allow the user to pass the looped ends of torso strap 210 and bicep strap 220 loosely around the user's body and arm before reconnecting the coupler with shoulder wrap 100 resting comfortably atop the shoulder. If the injury permits, the user can simply slide the connected bicep strap set 220 over the arm and pass the connected torso strap 210 over the head and under the opposite arm (FIG. 3). Once strap sets 210 and 220 are wrapped and connected around the user, the position of shoulder wrap 100 can be adjusted to the user's comfort (FIG. 4). With shoulder wrap 100 properly positioned, user pulls strap loops 232 to cinch strap lengths 230 down snugly securing the wrap to the user without the pad shifting about the user's shoulder (FIG. 5). The looped ends of strap lengths 230 overlap so that their hook and loop sections 236 adhere together securing shoulder wrap 100 in place about the user. Once secured on the user, fluid line 10 is connected to shoulder wrap 100 ready for hilotherapy (FIG. 6). To doff, fluid line 10 is disconnected from shoulder wrap 100 and couplers 250 on both strap sets 210 and 220 are disconnected allowing shoulder wrap 100 to fall freely from around the user.

One skilled in the art will note that the wraps of this invention provides several advantages from conventional hilotherapy practices. The strap assembly allows the user to don the wrap or pad without assistance even though the user has limited use of both arms or the use of only one arm. Since, both ends of the elastic torso and bicep straps can be connected to the cover with the straps loosely wrapped around the user, the wraps or pads can be donned and properly positioned atop the shoulder. Since the straps are connected to opposite side of the cover before tensioning, the wrap is held in place as the elastic straps are cinched down preventing the wrap or pad from shifting about the user. The quick connect couplings are readily accessible to the user and allow the wrap or pad to be quickly doffed. The use of hook and loop fastening materials as an interface between the strap, strap anchors and cover provides a secure light weight connection. The hook and loop fastener interface also allows the location and orientation of the elastic straps to be adjusted to fit the user and injury.

It should be apparent from the foregoing that an invention having significant advantages has been provided. While the invention is shown in only a few of its forms, it is not just limited but is susceptible to various changes and modifications without departing from the spirit thereof. The embodiment of the present invention herein described and illustrated is not intended to be exhaustive or to limit the invention to the precise form disclosed. It is presented to explain the invention so that others skilled in the art might utilize its teachings. The embodiment of the present invention may be modified within the scope of the following claims.

I claim:

1. A cold compression shoulder wrap comprising:
    a water bladder configured to overlie one shoulder and adjacent bicep of a user;
    a cover enclosing the bladder; and
    a strap assembly detachably connected to the cover for securely holding the wrap snuggly against the one shoulder and adjacent bicep using only the hand and arm of the opposite of the one shoulder,
    the strap assembly includes a torso strap set and a bicep strap set, each of the torso strap set and the bicep strap set includes a ring part, a strap anchor detachably connected to the cover and connected to the ring part, and an elongated length of elastic strapping having one end detachably connected to the cover and the opposite end operatively fitted to the ring part to allow the wrap to be drawn snuggly around the user by cinching the opposite end with the hand and arm of the opposite of the one shoulder when the wrap is donned by the user over the one shoulder.

2. The shoulder wrap of claim 1 wherein each of the torso strap set and the bicep strap set also includes a coupler detachably connecting the strap anchor and ring part.

3. The shoulder wrap of claim 1 wherein the length of elastic strapping of the torso strap set is adapted to wrap around the torso of the user when the wrap is donned by the user.

4. The shoulder wrap of claim 3 wherein the length of elastic strapping of the bicep strap set is adapted to wrap around the bicep of the user when the wrap is donned by the user.

5. The shoulder wrap of claim 1 wherein the cover has a pair of first sections adapted to overlie the shoulder and torso of the user and a pair of second sections adapted to overlie the bicep of the user.

6. The shoulder wrap of claim 5 wherein the length of elastic strapping of the torso strap set detachably connected between the pair of first sections of the cover.

7. The shoulder wrap of claim 5 the length of elastic strapping of the bicep set detachably connected between the pair of section sections of the cover.

8. The shoulder wrap of claim 5 wherein the bladder has a pair of first lobs disposable within the pair of first sections of the cover and a pair of second lobs disposable within the pair of second sections of the cover.

9. In a cold compression wrap including a water bladder configured to overlie one shoulder and adjacent bicep of a user and a cover enclosing the bladder, where the cover has a pair of first sections adapted to overlie the shoulder and torso of the user and a pair of second sections adapted to overlie the bicep of the user, a strap assembly for securely holding the wrap snuggly against the one shoulder and adjacent using only the hand and arm of the opposite of the one shoulder comprising:
    a torso strap set; and a bicep strap set, each of the torso strap set and the bicep strap set include a ring part, a strap anchor detachably connected to the cover, a coupler detachably connecting the strap anchor and ring part, and a length of elastic strapping having one end detachably connected to the cover and the opposite end operatively fitted to the ring part to allow the wrap to be drawn snugly around the user by cinching the opposite end with the hand and arm of the opposite of the one shoulder when the wrap is donned by the user over the one shoulder.

10. The shoulder wrap of claim 9 wherein the length of elastic strapping of the torso strap set is adapted to wrap around the torso of the user when the wrap is donned by the user, and the length of elastic strapping of the bicep strap set is adapted to wrap around the bicep of the user when the wrap is donned by the user.

11. The shoulder wrap of claim 10 wherein the length of elastic strapping of the torso set detachably connected between the pair of first sections of the cover, and the length of elastic strapping of the bicep set detachably connected between the pair of first sections of the cover.

* * * * *